United States Patent [19]

Agouridas et al.

[11] Patent Number: 5,030,715
[45] Date of Patent: Jul. 9, 1991

[54] NOVEL AMINOPIMELIC ACIDS

[75] Inventors: Constantin Agouridas, Paris; Patrick Fauveau, Livry-Gargan; Chantal Damais, Paris, all of France

[73] Assignee: Roussel Uclaf, Paris, France

[21] Appl. No.: 267,190

[22] Filed: Nov. 3, 1988

[30] Foreign Application Priority Data

Nov. 3, 1987 [FR] France .................. 87 15209

[51] Int. Cl.⁵ .................. A61K 31/195; C07C 229/02; C07K 5/08
[52] U.S. Cl. .................................... 530/331; 562/571
[58] Field of Search .......................... 530/331

[56] References Cited

PUBLICATIONS

Berges, D. A., et al, "Peptides of 2-Aminopimelic Acid: Antibacterial Agents that Inhibit Diaminopimelic Acid Biosynthesis", J. Med. Chem., 1986, 29:89–95.

*Primary Examiner*—Glennon H. Hollrah
*Assistant Examiner*—S. Mark Clardy
*Attorney, Agent, or Firm*—Bierman and Muserlian

[57] ABSTRACT

A) Compounds selected from the group consisting of a compound of the formula

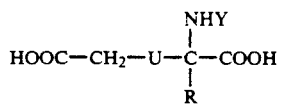

wherein U is

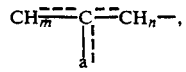

m and n are individually 1 or 2 of one, the dotted lines is a single double bond optionally of cis or trans configuration, a is selected from the group consisting of hydrogen, methyl and methylene, Y is selected from the group consisting of hydrogen, residue of an amino acid with an α-or ω-carboxyl and a peptide or 2,3 or 4 amino acids with the amine optionally acylated with an optionally unsaturated aliphatic carboxylic acid of 6 to 24 carbon atoms or alkylated with alkyl of 1 to 8 carbon atoms, R is selected from the group consisting of hydrogen, alkyl of 1 to 8 carbon, alkenyl and alkynyl of 2 to 8 carbon atoms optionally substituted with at least one halogen with the proviso that if Y is hydrogen, alanine or proline and if a is hydrogen, U contains a double bond; and B) their non-toxic, pharmaceutically acceptable salts with bases or acids, the alkyl esters of 1 to 6 carbon atoms and their primary and secondary amides having remarkable immunomodulatric properties and anti-bacterial activity.

30 Claims, No Drawings

NOVEL AMINOPIMELIC ACIDS

STATE OF THE ART

Related prior art includes French B.M. Patent No. 2,566,410 and Journal of Medicinal Chemistry, Vol. 29 (1986), p. 90, 93 and 94.

OBJECTS OF THE INVENTION

It is an object of the invention to provide the novel compounds of formula I and their derivatives and a novel process for their preparation.

It is another object of the invention to provide novel antibacterial compositions and a novel method of combatting bacterial infections in warm-blooded animals.

It is a further object of the invention to provide novel immunomodulatorily compositions and a method of their use.

These and other objects and advantages of the invention will become obvious from the following detailed description.

THE INVENTION

The novel compounds of the invention are selected from the group consisting of a compound of the formula

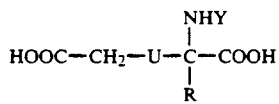

wherein U is

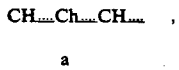

the dotted lines are a single double bond optionally of cis or trans configuration, a is selected from the group consisting of hydrogen, methyl and methylene, Y is selected from the group consisting of hydrogen, residue of an amino acid with an α- or ω- carboxyl and a peptide of 2, 3 or 4 amino acids with the amine optionally acylated with an optionally unsaturated aliphatic carboxylic acid of 6 to 24 carbon atoms or alkylated with alkyl of 1 to 8 carbon atoms, R is selected from the group consisting of hydrogen, alkyl of 1 to 8 carbon, alkenyl and alkynyl of 2 to 8 carbon atoms optionally substituted with at least one halogen with the proviso that if Y is hydrogen, alanine or proline and if a is hydrogen, U contains a double bond and their non-toxic, pharmaceutically acceptable salts with bases or acids, the alkyl esters of 1 to 6 carbon atoms and their primary and secondary amides.

Examples of U are

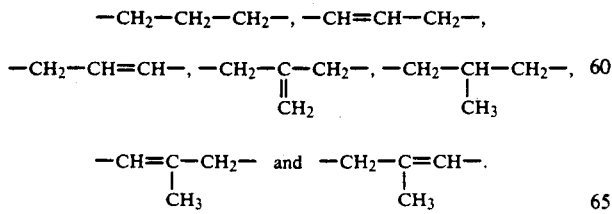

Examples of R are alkyl of 1 to 8 carbon atoms such as methyl, ethyl, n-propyl, isopropyl and butyl; alkenyl and alkynyl of 2 to 8 carbon atoms such as vinyl, allyl, ethynyl and propynyl; alkyl, alkenyl or alkynyl substituted with at least one halogen, preferably chlorine or fluorine such as $-CHF_2$, $-CH_2F$, $-CHCl_2$ and $-CH_2Cl$.

Examples of the amino acids of Y are preferably α-amino acids such as Ala, Val, Ival, Leu, Ile, Asp, Asn, Glu, Gln, Ser, Thr, Cys, Met, Lys, Arg, Phe, Tyr, Trp, His and Pro, Nva, Nle, Hyp, Orn with the acids being in the D or L form as well as Sar and Gly, all the acids optionally acylated or N-alkylated in the 2, 3- or 4 amino acid peptides constituted of said amino acids. By convention, the symbols of the λ-amino carboxylic acids may be acids in the D or L configuration. For example, Ala means alanine in its D form or L form.

Examples of the optionally unsaturated aliphatic carboxylic acids of 6 to 24, preferably 12 to 22 carbon atoms are stearic acid, palmitic acid, lauric acid, caprylic acid, myristic acid, α- or γ-linolenic acid, linoleic acid, arachidonic acid and docosopentaenoic acid.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as acetic acid, propionic acid, maleic acid, formic acid, succinic acid, tartaric acid, citric acid, oxalic acid, glyoxylic acid, aspartic acid, arylcarboxylic acids such as benzoic acid, alkanesulfonic acids such as methanesulfonic acid or ethanesulfonic acid or arylsulfonic acids such as benzenesulfonic acid or p-toluene sulfonic acid.

Examples of suitable bases for the non-toxic, pharmaceutically acceptable salts are inorganic bases like alkali metal and alkaline earth metal bases such as sodium hydroxide, potassium hydroxide, lithium hydroxide or calcium hydroxide or magnesium hydroxide or ammonium hydroxide and organic bases such as optionally substituted alkyl amines such as trimethylamine, propylamine, N,N-dimethyl-ethanol amine and tris(hydroxymethyl)methylamine and basic amino acids such as lysine or arginine as well as other bases such as glucosamine or procaine.

Among the preferred compounds of formula I are those wherein U is $-CH=CH-CH_2-$ or $-CH_2-CH=CH-$, those wherein Y is alanine, proline, lysine and α- or γ-glutamic acid, preferably lysine or alanine and those wherein R is hydrogen, methyl, $-CHF_2$, ethynyl or vinyl and their esters with alcohols of 1 to 6 carbon atoms, their primary and secondary amides and their non-toxic, pharmaceutically acceptable salts with acids or bases.

Specific preferred compounds of formula I are the products of Examples 6, 9, 13, 15 and 16. The primary amides are preferably

or secondary amides are preferably

and AlK is alkyl of 1 to 8 carbon atoms such as methyl, ethyl, n-propyl, isopropyl and butyl.

The novel process of the invention for the preparation of the compounds of formula I comprises reacting a compound of the formula

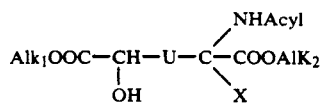 II wherein U has the above definition, $AlK_1$ and $AlK_2$ are individually alkyl of 1 to 8 carbon atoms, X is R or $-COOAlK_3$, $AlK_3$ is alkyl of 1 to 8 carbon atoms and acyl is acyl of an organic carboxylic acid of 1 to 8 carbon atoms with an alkylsulfonyl halide or arylsulfonyl halide of the formula

 III wherein $AlK_4$ is alkyl of 1 to 8 carbon atoms or aryl of 6 to 14 carbon atoms and Hal is a halogen and then with a reducing agent to obtain a compound of the formula

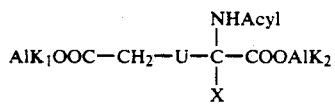 IV and optionally subjecting the latter to one or more of the following steps in any order: (a) deprotection of the amine function, (b) hydrolysis of ester groups and then to decarboxylation if X is $-COOAlK_3$, (c) reduction of the double bond, (d) esterification or salification with a base of the carboxyl groups, (e) salification of the amino groups with an acid and/or (f) amidification of the free amino groups with an amino acid or a peptide or 2, 3 or 4 amino acids whose amino groups are protected, then deprotection thereof.

In a preferred mode of the process of the invention, the compound of formula III is methanesulfonyl chloride and the reaction is effected in the presence of a condensation agent such as pyridine or in a neutral solvent such as methylene chloride in the presence of a base such as triethylamine. The reducing agent is preferably a metal such as zinc in the presence of sodium iodide in a basic solvent. The deprotection of the amino groups is preferably effected with a dilute mineral acid such as hydrochloric acid or with an organic acid such as trifluoroacetic acid in benzyl alcohol in the presence of an agent such as acetyl chloride. The hydrolysis of the ester groups is preferably effected by saponification with a mineral base such as sodium hydroxide or potassium hydroxide followed by treatment with an acid resin.

When X is $-COOAlK_3$, the ester hydrolysis is followed by a decarboxylation effected preferably with an organic acid such as 12N hydrochloric acid by heating in an organic a solvent such as ethanol or by treatment with an acid resin. A direct decarboxylation may be effected by the Krapcho procedure or by Keinan et al [J. Org. Chem., Vol. 51 (1986), p. 3165-3169]. The amidification is effected in the presence of condensation agents such as dicyclohexylcarbodiimide, N,N'carbonylidiimidazole or dialkylamides of sulfur containing acids such as N,N'-sulfinylbis (dimethylamine) or

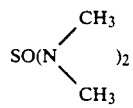

or by formation of a mixed anhydride with isobutyl chloroformate.

In a preferred embodiment of the process, a compound of the formula

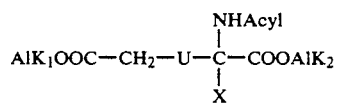 IV wherein $AlK_1$, $AlK_2$, Acyl and X have the above definition is subjected to the following steps in this order: (a) deprotection of the amine functions and hydrolysis of the ester functions to obtain a compound of the formula

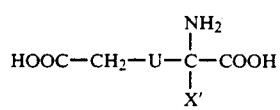 IA wherein X' is R or $-COOH$ and optionally the compound formula IA is amidified with an amino acid or a peptide of 2, 3 or 4 amino acids whose amine groups are protected, then in the case of a decarboxylation of X', then optionally deprotecting the amino groups of the product obtained.

The different steps of the process are realized depending upon the preferred modes of realization described.

In a variation of the process of the invention, a compound of the formula

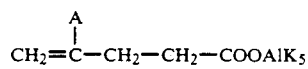 V wherein A is hydrogen or methyl and $AlK_5$ is alkyl of 1 to 8 carbon atoms is reacted with a compound of the formula

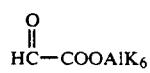 VI wherein $AlK_6$ is alkyl of 1 to 8 carbon atoms to obtain a compound of the formula

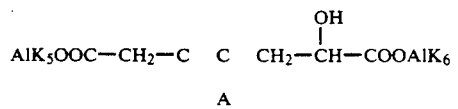 VII which is then reacted with a compound of the formula

 VIII wherein Hal is halogen and $AlK_7$ is alkyl of 1 to 3 carbon atoms or aryl of 6 to 14 carbon atoms to obtain a compound of the formula

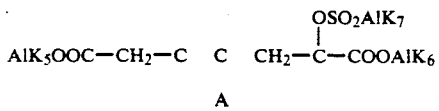

reacting the latter with an alkali metal azide to obtain a compound of the formula

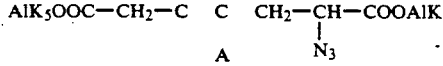

which is reduced and subjected to aqueous hydrolysis to obtain a compound of the formula

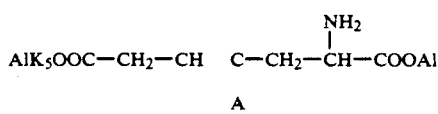

and optionally subjecting the latter to one or more of the following steps in any order: (a) hydrolysis of ester groups, (b) a modification of free amino group with an amino acid or peptide of 2, 3 or 4 amino acids whose amine groups are protected and the deprotection of said amino groups, (c) reduction of the double bond, (d) esterification or salification with a base of the carboxy and/or (e) salification of the amino groups by an acid.

In a preferred mode of this variation, the reactional the compounds of formulae V and VI is effected in the presence of ferric chloride or titanium tetrachloride or other known Lewis acids and the compound of formula VII is methanesulfonyl chloride used in the presence of a condensation agent such as pyridine or in a neutral solvent such as methylene chloride in the presence of a base such as triethylamine. The alkali metal azide is sodium azide or the azide may be diphenyl phosphorylazide (formed by direct passage from the alcohol to the azide) in the presence of triphenylphosphine and ethyl azodicarboxylate or potassium phthalimide in dimethylformamide. The reducing agent for reaction with the compound of formula X is triphenyl phosphpine or catalytic hydrogenation in the presence of palladized activated carbon poisoned with quinoline, for example. The aqueous hydrolysis agent of the phthalimide is a mineral base or hydrazine.

The following operations on the compound of formula XI is preferably effected by the preferred steps above for the different steps of hydrolysis of esters, modification of free amino group, reduction and esterification and salification.

The novel antibactericidal compositions of the invention are comprised of an antibacterially effective amount of at least one compound of formula I and its derivatives and an inert pharmaceutical carrier or excipient. The compositions having immunomodulatory poperties are comprised of an immunomodulatorily effective amount of at least one compound of formula I and its derivatives and an inert pharmaceutical carrier or excipient. The compositions may be in the form of tablets, dragees, gelules, granules, suppositories and injectable solutions or suspensions.

Examples of suitable excipients are talc, arabic gum, starch, lactose, magnesium stearate, cocao butter, aqueous and non-aqueous vehicles fatty bodies of animal or vegetable origin, paraffinic derivatives, glycols, diverse wetting agents, dispersants and emulsifiers and preservatives.

The compositions of the invention have remarkable immunomodulatory properties, especially for activation of human monocytes and production of monokines such as TNF (Tumor Necrosis Factor) and IL: (Interleukine 1) alone or in the presence of gamma IFN and antibacterial properties.

The compositions are useful in the treatment of autoimmune maladies such as non-specific attacks of organs (rhumatoid polyarthritis, erythemateous lupus, hemolytic anemia, auto-immune leucopenia, etc) or specific maladies of organs (thyroiditis, Basedom malady, Addison disease, plate sclerosis, pemphigus, hemorragic rectocolitis, certain nephropathies, etc). The compositions are also useful for the treatment of hemopathia, cancer, aids, viral and microbial infections, chronic and recurring conditions (bronchitis, grip, etc.) oral cavity maladies, etc. They may also be used as adjuvants for antiviral theraphy, antibacterial theraphy against bacteria germs and yeast and fungus (candida albicans) or in anticancer theraphy.

They are equally useful in the treatment of numerous secondary or acquired immunitary deficiencies or observed in the course of very diverse affections: deficiencies associated with metabolic troubles, of iatrogenic origin (corticoids, ionisant radiations) and deficiencies observed in large burns, etc.

The compositions of the invention are preferably used in association with gamma interferon for the production of monokines of the TNF type, IL1 for example, by the monocytes.

The novel method of treating bacterial infections in warm-blooded animals, including humans, comprises administering to warm-blooded animals an antibacterially effective amount of at least one compound of formula I and its derivatives. The method of inducing immunomodulatory activity in warm-blooded animals, including humans, comprises administering to warm-blooded animals an amount of at least one compound of formula I and its derivatives sufficient to induce immunomodulatory activity. The compounds may be administered orally, rectally or parenterally and the usual daily dose is 0.00066 to 0.66 mg/kg depending upon the condition treated, the specific compound and the method of administration. For example, the compound of Example 8 may be orally administered at a dose of 0.066 to 0.66 mg/kg for the prevention or treatment of fungal, viral or bacterial infections or for the treatment of tumors of diverse origins.

In the following examples there are described several preferred embodiments to illustrate the invention. However, it is to be understood that the invention is not intended to be limited to the specific embodiments.

EXAMPLE 1

2-amino-4-methylene-heptanedioic acid

STEP A: Diethyl 2-(formylamino)-(2-methyl-2-propenyl)-propandioate

A mixture of 40 g of potassium carbonate, 0.380 g of couronne 18 crown 6 ether catalyst and 39.9 g of chloromethylpropene was added to a solution of 30 g of ethyl formamidomalonate in 300 ml of acetonitrile and the mixture was refluxed for 3 hours and was filtered. The mixture was evaporated to dryness, cooled to 0° to −5° C. and was taken up in 10 ml of isopropyl ether. The mixture was filtered and the product was washed with isopropyl ether and dried under reduced pressure to obtain 25.2 g of the expected melting at ≈72° C.

STEP B: Triethyl 1-(formylamino-5-hydroxy-3-methylene-1,1-5-pentane tricarboxylat A solution of 26.5 g of ethyl glyoxylate in 180 ml of methylene chloride was added dropwise over 10 minutes to a solution of 84 g of ferric chloride in 180 ml of methylene chloride and after stirring for one hour, the mixture was cooled to −20° C. A solution of 34 g of the product of Step A in 180 ml of methylene chloride was added dropwise over 20 minutes and the mixture was stirred for one hour at −20° C. and then was poured into 300 ml of iced water. The mixture was extracted with methylene chloride and the organic phase was washed with 2N hydrochloric acid, then with aqueous sodium chloride, dried and evaporated to dryness under reduced pressure to obtain 56.5 g of the expected product melting at 68° C. after purification by chromatography on silica and elution with a 6-4 ethyl acetate-cyclohexane mixture.

STEP C: Triethyl 1-(formylamino)-3-methylene-1,1,5-pentane tricarboxylate 12 ml of methane sulfonyl chloride were added dropwise at 0° C. to a solution of 46 g of the product of Step B in 500 ml of pyridine and after stirring at room temperature for 3 hours, the mixture was poured into 400 ml of iced 4N hydrochloric acid and 200 ml of methylene chloride. The mixture was extracted with methylene chloride and the organic phase was washed with 4N hydrochloric acid, with saturated aqueous sodium bicarbonate solution and with aqueous sodium chloride, dried and evaporated to dryness under reduced pressure to obtain product A.

A suspension of 10.8 g of product A, 100 ml of dimethoxyethane, 10 ml of water, 18.5 g of sodium iodide and 16 g of zinc powder was refluxed for 6 hours and the suspension was cooled and filtered. The product was added to water and the mixture was extracted with methylene chloride. The organic phase was dried, filtered and evaporated to dryness to obtain 8.4 g of an oil. The oil was chromatographed over silica and eluted with a 1-1 cyclohexane-ethyl acetate mixture to obtain 5.75 g of the expected product.

NMR Spectrum (CDCl$_3$-ppm): Peaks at 1.25 (t), 1.27 (t), 4.12 and 4.26 (hydrogens of —CO$_2$CH$_2$=CH$_3$); at 8.18 (hydrogen of —COH); at 7.0 (hydrogens of NH$_2$); at 3.14 (s) (hydrogens of 2-methylene of pentane); at 4.8 and 4.9 (hydrogen of 3-substituted methylene of pentane); 2.2 to 2.45 (hydrogens of 4 and 5-methylenes of pentane).

STEP D: Triethyl 1-amino-3-methylene-1,1,5-pentane-tricarboxylate

A mixture of 6 g of the product of Step C, 60 ml of ethanol and 6 ml of concentrated hydrochloric acid was refluxed with stirring for 35 minutes and then the majority of the ethanol was evaporated. The mixture was cooled, water was added and the mixture was neutralized with sodium bicarbonate. The mixture was extracted with methylene chloride and the organic phase was washed with aqueous sodium chloride solution, dried, filtered and evaporated to dryness to obtain 5.2 g of an oil. The latter was chromatographed on silica and eluted with a 7-3 cyclohexane-ethyl acetate mixture to obtain the expected product.

NMR Spectrum (CDCl$_3$-ppm): Peaks at 1.25 (t) and 1.28 (t), 4.12 (q) and 4.23 (q) (hydrogens of —COOCH$_2$—CH$_3$); at 2.04 (s) (hydrogens of —NH$_2$); at 2.80 (s) (hydrogens of 2-methylene of pentane); 4.99 and 4.95 (hydrogen of 3-substituted methylene of pentane); at 2.28 m and 2.45 (hydrogens of 4 and 5 methylenes of pentane).

STEP E: 2-amino-4-methylene-heptanedioic acid 9.9 ml of a N sodium solution were added dropwise to a solution of 945 mg of the product of Step D in 10 ml of ethanol and the mixture was stirred at room temperature for 16 hours and then was evaporated to dryness under reduced pressure. The residue was taken up in 10 ml of water and 2 ml of pure acetic acid were added thereto. The mixture was stirred at 80° C. for 2 hours and was then evaporated to dryness to obtain 830 mg of product. The latter was passed through Dowex 50 W×8 resin and eluted with water and then 0.4N ammonium hydroxide. After 290 mg of residue were passed over cellulose and elution with a 9-1 methanol-water mixture, 160 mg of the expected product were obtained.

NMR Spectrum (D$_2$O-ppm): Peaks at 3.89 (dd J=4 and 10); (hydrogens of 2-methylene of heptanedioic acid); 2.51 (dd), 2.77 (dd) (hydrogens of 3-methylene of heptanedioic acid); at 5.00 and 5.02 (hydrogen of 4-substituted methylene of heptanedioic acid); at 2.3 to 2.5 (hydrogens of 5 and 6 methylene of heptanedioic acid).

EXAMPLE 2

2-(L-alanylamino)-4-methylene-heptanedioic acid

STEP A: Triethyl 1-[[N-(1,1-dimethylethoxycarbonyl)-L-alanyl]-amino]-3-methylene-1,1,5-pentanetricarboxylate A solution of 945 mg of the product of Step D of Example 1, 30 ml of dimethoxyethane and 621 mg of Boc-L-alanine was cooled to 0° C. and 678 mg of dicyclohexylcarbodiimide were added in small fractions over 10 minutes. The mixture was stirred at 0° C. for 16 hours. After filtering, the filtrate was evaporated to dryness under reduced pressure and chromatography was carried out on silica. Elution with a cyclohexane-ethyl acetate mixture (7-3) yielded 1.3 g of the expected product with a specific rotation of [α]$_D$=−22°±2° (c=0.7% in CH$_2$Cl$_2$).

NMR Spectrum CDCl$_3$ in ppm: H of CO$_2$CH$_2$CH$_3$ groups:

$$\begin{cases} 1.25\ (t)-1.26\ (t) \\ 4.05\ to\ 4.35 \end{cases}$$

H of the CH$_3$'s of

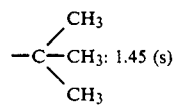
—C—CH$_3$: 1.45 (s)

H of the CH of the L-alanyl group: 4.05 to 4.35 ppm; H of the CH$_3$ of the L-alanyl group: 1.35 (d); H of the CH$_2$ in position 2 of the pentane: 3.12; H of the substituted methylene in position 3 of the pentane: 4.77 and 4.86; H of the CH$_2$'s in positions 4 and 5 of the pentane: 2.23–2.40.

STEP B: 2-(L-alanylamino)-4-methylene heptanedioic acid 3.9 ml of a N sodium hydroxide solution were added dropwise at 0° C. to a solution of 580 mg of the product of Step A and 5 ml of ethanol. The reaction mixture was stirred for 4 hours and then was evaporated to dryness under reduced pressure. The residue was taken up in ethanol and the salt formed was separated, washed and dried to obtain 580 mg of a product which was dissolved in 2 ml of water. Amberlyst 15 resin was added to the solution to obtain a pH of 3 and the solution was filtered, washed with water and evaporated to dryness under reduced pressure. The residue was taken up in 2.5 ml of water and 4.5 ml of acetic acid. The reaction mixture was stirred for 2 hours at 80° C. and evaporated to dryness under reduced pressure. 370 mg of a resin were obtained which was purified by chromatography on silica and elution with a propanol - water mixture (8-2) to obtain 250 mg of blocked amine in the form of t-butyl carbamate to which 2.5 ml of methylene chloride and 1 ml of trifluoroacetic acid were added. The mixture was stirred for 3 hours at ambient temperature and evaporated to dryness under reduced pressure. The residue was purified by chromatography on siica and elution with a propanol - water mixture (8-2). After it was passed through Dowex resin 50 W×8, elution was carried out with 250 ml of distilled water, then with 0.4N ammonium hydroxyide to obtain 126 mg of the expected product with a specific rotation of $[\alpha]_D = +3° \pm 1.5°$ (c=0.6% in H$_2$O).

NMR Spectrum D$_2$O, in ppm: H of the CH$_3$ of the L-alanyl group: 1.49 (d) resolved; H of the CH of the L-alanyl group: 4.09 (q) resolved; H of the CH in position 2 of the heptanedioic acid: 4.36; H of the substituted methylene in position 4 of the heptanedioic acid: 4.85 and 4.89; H of the CH$_2$'s in positions 5 and 6 of the heptanedioic acid: 2.2 to 2.7.

EXAMPLE 3

2-[(γ-D glutamyl)-amino]-4-methylene heptanedioic acid

STEP A: Triethyl 3-methylene-1-[[0-methyl-N-(trifluoroacetyl)-γ-D-glutamyl]-amino]-1,1,5-pentanetricarboxylate A solution of 1.27 g of the product of Step D of Example 1, 50 ml of dimethoxyethane and 1.22 g of 1-methyl (N-trifluoroacetyl)-D-glutamate was cooled to 0° C. and 1.06 g of dicyclohexylcarbodiimide were added in small fractions. The mixture was stirred for 16 hours at 0° C. and the precipitate formed was filtered off. The filtrate was evaporated to dryness under reduced pressure to obtain 2.4 g of residue which was chromatographed on silica. Elution with a cyclohexane - ethyl acetate mixture (6-4) yielded 1.6 g of the expected product with a Rf=0.3 and a specific rotation of $[\alpha]_D = +11.5° \pm 1.5°$ (c=0.65% in CH$_2$Cl$_2$).

NMR Spectrum CDCl$_3$ in ppm: H of CO$_2$CH$_2$CH$_3$ groups: 1.18 to 1.31; 4.11 (q) and 4.25 (q); H of the CH$_3$ of the CO$_2$CH$_3$: 3.77 (s); H of the CH of the gamma-glutamyl: 4.50 (dt); H of the CH$_2$ in position 2 of the pentane: 3.11 (s); H of the substituted methylene in position 3 of the pentane: 4.75 and 4.87; H of the CH$_2$'s in positions 4 and 5 of the pentane: 2.05 to 2.50.

STEP B: 2-[γ(D-glutamyl)-amino]-4-methylene heptanedioic acid 11.8 ml of N sodium hydroxide were added at 0° C. to a solution of 1.1 g of the product of Step A and 50 ml of ethanol and the reaction mixture was stirred for 16 hours. After evaporating to dryness, the residue was taken up in 10 ml of water and 2 ml of pure acetic acid. The mixture was stirred for 4 hours at 80° C. and then was evaporated to dryness under reduced pressure. The 1.8 g of product was purified on silica and eluted with an ethanol - ammonia mixture (90-10) to obtain 510 mg of crude product which was purified by taking up in ethanol until a white precipitate was obtained. After separating and evaporating to dryness under reduced pressure, a product was obtained which was dissolved in watre, filtered and lyophilized to obtain 280 mg of the expected product after 2 successive lyophilizations with a specific rotation of $[\alpha]_D = -12° \pm 1.5°$. (c=0.7% in H$_2$O).

NMR Spectrum D$_2$, in ppm: H of the substituted methylene in position 4 of the heptanedioic acid: 4.86 to 488; H of the CH in position 2 of the heptanedioic acid: 4.33; H of the CH in the D-glutamyl: 3.76; H of the CH$_2$'s in positions 5 and 6 of the heptanedioic acid: 2.05 to 2.70.

EXAMPLE 4

2-amino-3-heptenedioic acid

STEP A: Triethyl 1-(formylamino)-2-penten-1,1,5-tricarboxylate 4.2 g of sodium iodide and 3.7 g of zinc were added to a solution of 2.4 g of the product A of Step C of Example 1 and the reaction medium in dimethoxyethane was refluxed in the presence of water with stirring for 2 hours. 50 ml of water were added and after filtration, extraction was carried out with methylene chloride. The extracts were dried and evaporated to dryness under reduced pressure to obtain 2.3 g of crude product which was chromatographed on silica. Elution with a cyclohexane ethyl acetate mixture (5-5) yielded 1.6 g of the expected product.

NMR Spectrum: H of the formyl: 8.1 ppm; ethylenic H in position 2: 6.0–6.3 ppm; ethylenic H in position 3: 5.7 ppm; H of the CH$_2$'s in positions 4 and 5: 2.3 to 2.5 ppm.

STEP B: 2-amino-3-heptenedioic acid 0.25 ml of 12N hydrochloric acid were added to a solution of 0.5 g of the product of Step A in 5 ml of ethanol. The mixture was refluxed for one hour, then cooled to ambient temperature and 20 ml of water were added. The ethanol was evaporated under reduced pressure and the mixture was neutralized with a 10% solution of potassium bicarbonate. Extraction was carried out with ethyl acetate and the organic phases were dried over magnesium sulfate and evaporated to dryness to obtain 0.4 g of crude product.

0.34 g of the product were dissolved in 10 ml of ethanol at 0° C., and 3.2 ml of a N sodium hydroxide solution was added dropwise. The mixture was stirred for 16 hours at ambient temperature and then evaporated to dryness. The residue was taken in 5 ml of water and 0.2 ml of acetic acid were added. The solution was stirred for 16 hours at ambient temperature, and then evaporated to dryness. The product was purified by passing through cellulose (eluents: propanol - water 9-1, 8-2 and 7-3), filtering through exclusion gel, and passing through ion-exchange resin to obtain 0.110 g of the expected product.

NMR Spectrum (D$_2$O in ppm): H of the CH in position 2: 4.20; ethylenic H's: 5.59 dd J=8 and 15.5; 5.98 d J=15.5 and 6; H of the CH$_2$'s in positions 5 and 6: 2.25 to 2.42.

EXAMPLE 5

6-amino-3-heptenedioic acid

STEP A: Ethyl (7) methyl (1) 6-hydroxy-3-heptenedioate

A solution of 40 g of methyl 4-pentenoate in methylene chloride was added at 0°/+6° C. over 15 minutes to a suspension of 71.5 g of ethyl glyoxylate in one liter of methylene chloride and 115 g of ferric chloride. The mixture stood for 15 minutes at 0°/+5° C. and then was allowed to return to ambient temperature and poured over ice. After decanting, the CH$_2$Cl$_2$ phase was washed with N hydrochloric acid and after drying over magnesium sulfate and evaporation, 84 g of crude product were obtained which was purified on silica (eluent: cyclohexane - ethyl acetate (7-3)) to obtain a 70% yield of the expected product.

STEP B: Ethyl (7) methyl (1) 6-[(methylsulfonyl)-oxy]-3-heptenedioate 1.5 g of the product of Step A were dissolved in 15 ml of methylene chloride at ambient temperature and 15.6 ml of pyridine and 0.7 ml of methane sulfonyl chloride were added. The mixture was stirred for 16 hours at ambient temperature and the mixture was poured slowly into a 6N solution of hydrochloric acid with methylene chloride added. Extraction was carried out with methylene chloride, followed by washing with a sodium bicarbonate solution, drying and evaporating to dryness. The residue was purified by chromatography on silica and elution with a methylene chloride - ethyl acetate mixture (9-1). The fractions containing the desired product were combined and brought to dryness to obtain 0.3 g of the expected product with a Rf=0.45 in the system CH$_2$Cl$_2$ AcOEt (85-15).

NMR Spectrum in ppm: H of SO$_2$CH$_3$: 3.15; H of CO$_2$CH$_2$CH$_3$: 1.31 and 4.26; H of the CH in position 6: 5.05; H of the CH$_2$ in position 5: 2.55 to 2.8; ethylenic H's: 5.56 and 5.74; H of CO$_2$CH$_3$: 3.68; H of the CH$_2$ in position 2: 3.08.

STEP C: (7) ethyl and (1) methyl 6-azido-3-heptenedioate 1.6 g of the product of Step B were dissolved in 20 ml of dimethylformamide and 0.39 g of sodium nitride were added. The mixture was stirred for 16 hours at ambient temperature and the dimethylformamide was evaporated at 35° C. maximum. The residue was taken up in methylene chloride and the solution was washed with a 10% solution of sodium bicarbonate and then with salt water. After drying and evaporating to dryness, 1.25 g of residue were obtained which was chromatographed on silica and eluted with an ethyl acetate - cyclohexane mixture (3-7). The fractions of interest were evaporated to dryness to obtain 1.03 g of the expected product with a Rf=0.3 in a cyclohexane - ethyl acetate mixture (8-2).

NMR Spectrum: ethylenic H's 5.55 and 5.75 ppm; H of CO$_2$CH$_3$: 3.69 ppm; H of the CH$_2$ in position 2: 3.08 ppm; H of the CH$_2$ in position 5: 2.45 to 2.65 ppm; H of CO$_2$Et: 1.31 ppm and 4.25 ppm; H of the CH in position 6: 3.88 ppm.

STEP D: (7) ethyl and (1) methyl 6-amino-3-heptenedioate 21.1 g of the product of Step C were dissolved in 350 ml of tetrahydrofuran and after cooling to 0° C., 27.5 g of triphenyl phosphine were added. The mixture was stirred at ambient temperature for 5 hours and 23.6 ml of water were added. The mixture was stirred at ambient temperature for 16 hours and the tetrahydrofuran was evaporated. The residue was taken up in methylene chloride and extraction was done twice with a 2N hydrochloric acid solution. After neutralizing with sodium bicarbonate, extraction was carried out with methylene chloride. The extracts were washed with salt water, dried and evaporated to dryness to obtain 16.2 g of the expected product with a Rf=0.25 in ethyl acetate - ethanol (9-1).

NMR Spectrum CDCl$_3$: H of NH$_2$: 1.61 ppm; H of CH in position 6: 3.51 ppm; H of CO$_2$Et: 1.28 and 4.18 ppm; H of CH$_2$ in position 5: 5.52 and 5.68 ppm; H of CH$_2$ in position 2: 3.07 ppm.

STEP E: 6-amino-heptenedioic acid 1 g of the product of Step D were dissolved in 10 ml of ethanol and 5.1 ml of a 2N solution of sodium hydroxide were added. The mixture was stirred for 16 hours at ambient temperature and the mixture was evaporated to dryness under reduced pressure. The product obtained was neutralized with resin Dowex 50 W×8 and the fractions containing the desired product were evaporated to dryness. A product was obtained which was lyophilized in 150 ml of filtered, double distilled water to obtain 660 mg of the expected product with a Rf=0.5 in a BuOH—AcOH—H$_2$O mixture (4-2-2).

NMR Spectrum D$_2$O: ethylenic H's: 5.46 ppm–5.80 ppm; H of the CH$_2$ in position 5: 2.49 to 2.76 ppm; H of the CH in position 6: 3.79 ppm; H of the CH$_2$ in position 2: 2.98 ppm.

EXAMPLE 6

6-(L-alanylamino)-3-heptenedioic acid

STEP A: (7) ethyl and (1) methyl 6-[[N-(1,1-dimethylethoxy)-carbonyl]-L-alanylamino]-3-heptenedioate 3.9 g of the product of Step D of Example 5 were dissolved in 200 ml of dimethoxyethane and 3.63 g of N-Boc-L-alanine were added. The mixture was cooled to −5°/0° C. and after addition of 3.99 g of dicyclohexylcarbodiimide, the mixture was vigorously stirred for 16 hours at 0° C. followed by filtering and evaporating to dryness. The residue was taken up in dimethoxyethane and filtered, then evaporated to dryness and taken up in methylene chloride. After washing with a saturated solution of sodium bicarbonate, then with salt water, drying and evaporating to dryness, 7.7 g of crude product were obtained which was chromatographed on silica. Elution with a cyclohexane - ethyl acetate mixture (7-3) yielded 5.4 g of the expected product with a specific roation of [α]=−18.5°±1° (c=1.6% in CH$_2$Cl$_2$).

NMR Spectrum CDCl$_3$: H of the CH$_3$'s of C(CH$_3$)$_3$: 1.45 ppm; H of CO$_2$Et

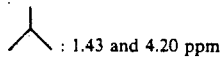 : 1.43 and 4.20 ppm

H of

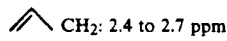 CH₂: 2.4 to 2.7 ppm

H of the CH₂ in position 2: 3.05 ppm

H of CO₂CH₃: 3.17 and 6.68 ppm; Ethylenic H's: 5.42 and 5.62 ppm; H of the CH₃ of the L-alanyl fragment: 1.36 and 1.35 ppm.

STEP B: 6-(L-alanylamino)-3-heptenedioic acid 790 mg of the product of Step A were dissolved in 20 ml of ethanol at ambient temperature and after cooling in an ice bath, 2.4 ml of a 2N sodium hydroxide solution were added. The mixture was stirred at ambient temperature for 2 hours 30 minutes and the pH 6 was adjusted to 6 with a concentrated solution of hydrochloric acid. The mixture was evaporated to dryness and the residue was taken up in 10 ml of dioxane and 1 ml of a 12N hydrochloric acid solution was added. The suspension was stirred for 30 minutes at 70° C. and the precipitate was filtered. The filtrate was evaporated to dryness and the residue was taken up in 2 ml of water. The pH was adjusted to 6 with N sodium hydroxide, followed by passing through ion-exchange resin (H+), eluting with water and then with 0.5N ammonia. The fractions containing the desired product were evaporated to dryness to obtain 420 mg of a product which was taken up in double distilled and filtered water and lyophilized to obtain 370 mg of the expected product with a Rf=0.5 eluting with a BuOH—AcOH—H₂O mixture (4-2-2) and having a specific rotation of $[\alpha]_D = -4° \pm 1°$ (c=1% in 5NHCl).

NMR Spectrum CD₃OD, (ppm): Ethylenic H's: 5.42-5.65; H of

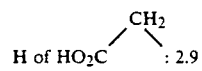

H of the CH₂ in position 2: 2.37-2.64; H of the CH in position 6: 4.29; H of the CH of the L-alanyl fragment: 3.95; H of the CH₃ of the L-alanyl fragment: 1.47.

EXAMPLE 7

(7) ethyl and (1) methyl 6-[[N[(1-oxo-octadecyl)-L-alanyl]-0-methyl-γ-D-glutamyl]-amino]-3-heptenedioate A solution of 1.99 g of 1-methyl [N-(1-oxo-octadecyl)-L-alanyl]-D-glutamate and 70 ml of anhydrous tetrahydrofuran was cooled to 10°-12° C. and 1.16 ml of triethylamine and 0.6 ml of isobutyl chloroformate were added. The mixture was stirred at 10°-12° C. for 35 minutes and 0.86 g of the product of Step D of Example 5 and 10 ml of anhydrous tetrahydrofuran were added. The mixture was stirred at ambient temperature for 2 hours and ice was added. Extraction was carried out with methylene chloride and the extracts were washed with a N hydrochloric acid solution and with salt water, dried and evaporated to dryness under reduced pressure to obtain 2.9 g of crude product which was purified by chromatography on silica. Elution with a CH₂Cl₂-MeOH mixture (98-2) yielded 1.8 g of the expected product melting at 110° C. and having a specific rotation of $[\alpha]_D = -14.5° \pm 2°$ (c=0.5% in methylene chloride).

NMR Spectrum CDCl₃ ppm: 0.88 (t): CH₃ of the chain; 1.25: (CH₂)ₙ and CH₃ ethyl; 1.38-1.39: CH₃—CH; 1.9 to 2.4: (CH₂)₂—CH and CH₂—C═O; 2.55: ═C—CH₂—CH; 3.06: ═C—CH₂—C═O; 3.65-3.68 and 3.73: CO₂CH₃; 4.21: —CH₂—CH₃;

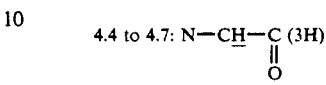

5.46 and 5.67: ethylenic H's (J=15 Hz)

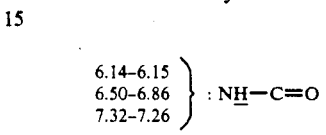

EXAMPLE 8

6-[[N-[(1-oxo-octadecyl)-L-alanyl-γ-D-glutamyl]-amino]-3-heptenedioic acid (sodium salt)

3.6 ml of a N sodium hydroxide solution were added at 0° C. to a solution of 800 mg of the product of Example 7 and 15 ml of ethanol. The mixture was stirred for 2 hours at ambient temperature and then brought to dryness under reduced pressure without heating. The residue was taken up in water, filtered and lyophilized to obtain 775 mg of the expected product melting at 200° C. (m.p. not very clear) and having a specific rotation of $[\alpha]_D = -26° \pm 2°$ (c=0.5% in H₂O).

NMR Spectrum D₂O (ppm): 0.89 (t): CH₃ of the chain; 1.40 (t): CH₃—CH; 1.92 to 2.5: (CH₂)₂—CH; C═C—CH₂—CH; —CH₂—C═O;

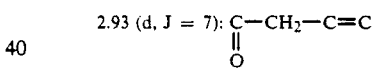

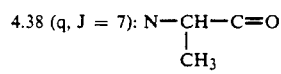

4.17 (m): the other N—CH—C═O's

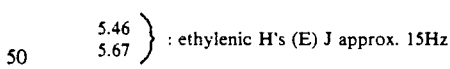

EXAMPLE 9

6-(L-lysylamino)-3-heptenedioic acid

STEP A:

N,N'-bis[(1,1-dimethylethoxy)-carbonyl]-L-lysine 1.46 mg of lysine were dissolved in a solution of 0.4 g of sodium hydroxide pastilles in 1 ml of water and 2 ml of tertbutanol were added. (BOC)₂O was introduced dropwise and the suspension was stirred for 4 hours at ambient temperature. After dilution with water, the pH was brought to 4 with a potassium bisulfate solution (10 g/300 ml of water). Extraction was carried out with ethyl acetate, followed by washing with salt water to neutrality, drying and evaporating to dryness to obtain 2.35 g of the expected product with a specific rotation of $[\alpha]_D = +12° \pm 1°$ (c=1% in H₂O).

NMR Spectrum CDCl₃: H of the tert-butyl groups: 1.45–1.47–1.52 ppm; H of the CH₂ in position 6 of the lysine: 3.12 ppm; H of the CH in position 2 of the lysine: 4.12 and 4.30 ppm.

STEP B: (7) ethyl and (1) methyl 6-[[N,N'-bis-[(1,1-dimethylethoxy)-carbonyl]-L-lysyl]-amino]-3-heptenedioate 1.74 g of the product of Step A and 1.076 g of (7) ethyl and (1) methyl 6-amino-3-heptenedioate were dissolved in 80 ml of dimethoxyethane and after cooling to 0° C., a solution of 1.03 g of dicyclohexylcarbodiimide in 20 ml of dimethoxyethane was introduced, followed by stirring for 16 hours at 0° C. Filtering was carried out, and the filtrate was evaporated to dryness to obtain 2.9 g of crude product which was purified by chromatography on silica. Elution with an ethyl acetate - cyclohexane mixture (1-1) was effected and the fractions containing the product were evaporated to dryness to obtain 1.78 g of the expected product with a specific rotation $[\alpha]_D = -14° \pm 2°$ (c=0.65% in CH₂Cl₂).

NMR Spectrum CDCl₃ (ppm): H of C(CH₃)₃: 1.44–1.45; H of CO₂CH₃: 3.68–3.69; H of CO₂CH₂CH₃: 4.20 (m); H of CO₂CH₂CH₃: 1.28 (t); H of the CH₂ in position 2 of the heptenedioic fragment: 3.05 (d); H of the CH₂ in position 5 of the heptenedioic fragment: 2.55 (m); H of the CH's in position 2 of the lysyl fragment and in position 6 of the heptenedioic fragment: 4.1–4.60.

STEP C: Sodium salt of 6-[[N,N'-bis[(1,1-dimethylethoxy)-carbony]-L-lysyl]-amino]-3-heptenedioic acid 6 ml of a N sodium hydroxide solution were added at 0° C. to a solution of 1.47 g of the product of Step B and 25 ml of ethanol. The mixture was stirred for 90 minutes at 0° C., then for 150 minutes at ambient temperature. Evaporation was carried out at ambient temperature under reduced pressure to obtain 1.57 g of the expected product.

NMR Spectrum D₂O (ppm): H of the C(CH₃)₃'s: 1.43–1.45; H of the CH₂ in position 6 of the lysyl fragments: 3.08 (t); H of the CH₂'s in position 2 of the lysyl fragments and in position 6 of the heptenedioic fragment: 4.03 (m)–4.22 (m); Ethylenic H's 5.14 (m)–5.60 (m); H of the CH₂ in position 2 of the heptenedioic fragment: 2.93 (d).

STEP D: 6-(L-lysylamino)-3-heptenedioic acid 1.16 g of the product of Step C were dissolved in 17 ml of dioxane and 1.7 ml of a solution of concentrated hydrochloric acid were added. The mixture was heated at 70° C. for 30 minutes and then was evaporated to dryness. After diluting with water, the pH was brought to 6 by the addition of sodium bicarbonate. Purification is carried out by passing through ion-exchange resin Dowex 50 W×8 and eluting with water and then with 0.2N ammonia. After evaporating to dryness and lyophilizing, 536 mg of the expected product with a specific rotation $[\alpha]_D = +15° \pm 1°$ (c=1% in H₂O) were obtained.

NMR Spectrum D₂O (ppm):

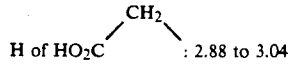

Ethylenic H's: 5.46–5.69

H of the CH₂ in position 2 of the heptenedioic fragment: 2.4 to 2.7; H of the CH in position 6 of the heptenedioic fragment: 4.25; H of the CH in position 2 of the lysyl fragments: 4.02; H of the CH₂ in position 6 of the lysyl fragments: 2.88 to 3.04.

EXAMPLE 10

6-[(L-alanyl-γ-D-glutamyl)-amino]-3-heptenedioic acid

STEP A: Ethyl (7) methyl (1) 6-[[N-(trifluoroacetyl)-L-alanyl](0-methyl)-γ-D-glutamyl]-amino]-3-heptenedioate 0.62 ml of isobutyl chloroformate were added at 12° C. to a solution of 1.44 g of 1-methyl N-[N-(trifluoroacetyl)-L-alanyl]-D-glutamate, 1.2 ml of triethylamine and 70 ml of tetrahydrofuran. The mixture was stirred for one hour and a solution of 0.9 g of the product of Step D of Example 5 in 30 ml of tetrahydrofuran was added dropwise. The solution was stirred for one hour at ambient temperature and 20 ml of water were added. Extraction was carried out with methylene chloride and the methylene chloride phase was washed with 20 ml of N hydrochloric acid, dried and evaporated to dryness to obtain 2.2 g of a product which was purified by chromatography on silica. Elution with a methylene chloride - ethyl acetate mixture (4-6) yielded 1.32 g of the expected product which was triturated with isopropyl ether to obtain 1.12 of the expected product melting at 70° C.

NMR Spectrum CDCl₃ (ppm): H of CO₂CH₂CH₃: 1.29 (d)

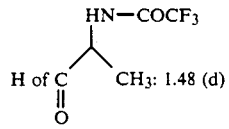

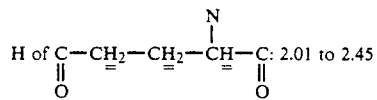

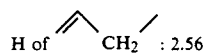

H of=CH—CH₂—CO₂CH₃: 307
H of CO₂CH₃: 3.69–3.70 and 3.75

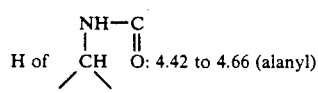

Ethylenic H's: 5.42 and 5.66 (m)
H of the NH's: 6.40 (d), 6.50 (d), 7.46 and 7.88.

STEP B: 6-[(L-alanyl-γ-D-glutamyl)-amino]-3-heptenedioic acid 6.4 ml of a solution of N sodium hydroxide were added dropwise to a solution of 0.8 g of the product of Step A and 16 ml of ethanol at 0° C. The solution was stirred for 16 hours at ambient temperature and then was brought to pH of 7 with acetic acid. The solution was concentrated under reduced pressure and 5 ml of water were added to the residue. Purification was carried out by passing through ion-exchange resin Dowex 50 W×8 and eluting with 0.2N ammonia, followed by lyophilization to obtain 0.545 of the expected product with a specific rotation of $[\alpha]_D = +4° \pm 2°$ (c = 1% in $H_2O$).

NMR Spectrum: H of the $CH_3$ of the alanyl fragment: 1.47 (d)–1.49 (d); H of the $CH_2$ in position 2 of the heptenedioic fragment: 2.91 (d); H of the $CH_2$ in position 5 of the heptenedioic fragment and of the $CH_2$'s of the glutamyl fragment: 1.89 to 2.60; H of the CH of the alanyl fragment: 3.94; H of the CH of the glutamyl fragment: 4.15 to 4.30; Ethylenic H's: 5.45 and 5.66.

EXAMPLE 11

2-amino-2-methyl-4-methylene heptanedioic acid

STEP A: Dimethyl (2-methyl-2-propenyl)-propanedioate 50 g of diethyl 2-methyl malonate were dissolved in 500 ml of acetonitrile and 80 g of potassium carbonate, 800 mg of crown 18 crown 6 ether and then 75 g of 3-chloro-2-methyl-1-propene were added. The mixture was stirred at reflux for 8 hours. The insoluble part was filtered off and the filtrate was concentrated to dryness. The residue was chromatographed on silica and eluted with a cyclohexane - ethyl acetate mixture (9-1) to obtain 28.3 g of pure product and 32 g of a mixture. The latter was chromatographed on silica and elution with a cyclohexane - ethyl acetate mixture (9-1) yielded another 16.5 g of the expected product with a Rf=0.3 in cyclohexane - ethyl acetate (9-1).

STEP B: Monoethyl methyl-(2-methyl-2-propenyl)-propanedioate

A mixture of 27 g of diethyl methyl-(2-methyl-2-propenyl)-propanedioate in 250 ml of ethanol was cooled to 0° C. and 65 ml of 2N sodium hydroxide were added dropwise. The mixture was stirred for 24 hours at ambient temperature. The mixture was poured into 30 ml of 6N iced hydrochloric acid. The mixture was extracted with ethyl ether and the extract was evaporated to dryness. The residue was taken up in methylene chloride and the solution was extracted with an aqueous solution of 10% sodium bicarbonate, followed by acidification with concentrated hydrochloric acid and extraction with ethyl acetate. The organic phase was washed with salt water, dried and evaporated to dryness to obtain 24 g of the expected product with a Rf=0.4 in $CH_2Cl_2$—MeOH (9-1).

STEP C: Ethyl 2,4-dimethyl-2-[(methoxycarbonyl)-amino]-4-pentenoate 27.5 g of the product of Step B were dissolved in 150 ml of thionyl chloride and the mixture was refluxed for 3 hours. The mixture was evaporated to dryness under reduced pressure to obtain 30 g of acid chloride. 14.5 g of the latter were dissolved in 100 ml of acetone and the solution was cooled to 0° C. 5.187 g of sodium azide in solution in 40 ml of water were added dropwise followed by stirring for one hour at 0° C. The acetone was evaporated off, followed by extraction with ether, drying and evaporation to dryness to obtain 25 g of azide. The latter was dissolved in 200 ml of methanol and the mixture was refluxed with stirring for 16 hours and then was evaporated to dryness. The residue was taken up in methylene chloride and the organic phase was washed with salt water, dried, evaporated to dryness to obtain 22 g of crude product. The residue was chromatographed on silica and eluted with a cyclohexane - ethyl acetate mixture (8-2) to obtain 11.2 g of the expected product with a Rf=0.4 in cyclohexane - ethyl acetate (8-2).

STEP D: Diethyl 6-hydroxy-2-[(methoxycarbonyl)-amino]-2-methyl-4-methyl-heptanedioate A solution of 9.9 g of ethyl glyoxylate in 150 ml of methylene chloride was added dropwise to a suspension of 30.5 g of ferric chloride in 150 ml of methylene chloride and the mixture was stirred for 30 minutes at ambient temperature. After cooling to $-60°$ C., 11.1 g of the product of Step C in 150 ml of methylene chloride were added dropwise. The mixture was allowed to return to $-30°$ C. and was poured into 400 ml of iced water. The mixture was extracted with methylene chloride and the organic phase was washed with water, with a 10% aqueous solution of sodium bicarbonate and then with salt water, dried and evaporated to dryness to obtain 15.3 g of crude product corresponding to a mixture of 65% of the expected product and 35% of 4-methyl-heptene. After passing through silica (eluent: cyclohexane - ethyl acetate (7-3), 11.4 g of the purified mixture was obtained with a Rf=0.25 in cyclohexane - ethyl acetate (6-4).

STEP E: Ethyl 2-[methoxycarbonyl)-amino]-2-methyl-4-methylene-6-[(methylsulfonyl)-oxy]-heptanedioate 11.4 g of the product of Step D were dissolved in 150 ml of pyridine and after cooling to 0° C., 4.9 g of methanesulfonyl chloride were added. The mixture was stirred for one hour at 0° C. and 5 hours at ambient temperature and was then poured into 6N hydrochloric acid and extracted with ethyl acetate. The organic phase was washed with 6N hydrochloric acid, with a 10% aqueous solution of sodium bicarbonate and then with salt water. After drying and evaporating to dryness, the residue was chromatographed on silica and eluted with a methylene chloride - ethyl acetate mixture (9-1) to obtain 6 g of the expected product, 6 g of "4-methylene heptane" and "4-methyl heptene" mixture and 0.7 g of "4-methyl heptene". After a second chromatography of the mixture fraction under the same conditions, 3.5 g of the expected product, 1 g of mixture and 1.1 g of the product 4-methylheptene were obtained. Rf in $CH_2Cl_2$=ethyl acetate (9-1): 0.4 for the product 4-methylene heptane, 0.35 for the product 4-methyl heptene.

STEP F: Diethyl 2-[(methoxycarbonyl)-amino]-2-methyl-4-methylene heptanedioate 1.5 g of the product of Step E were dissolved in 20 ml of dimethoxyethane and then 2 ml of water, 2.75 g of sodium iodide and 2.4 g of zinc were added successively. The mixture was refluxed for 8 hours with stirring and after filtering, the insoluble part was washed with water and with methylene chloride. The filtrate was extracted with methylene chloride and the organic phase was washed with salt water, dried and evaporated to dryness. The residue was chromatographed on silica and eluted with a cyclohexane - ethyl acetate mixture (8-2) to obtain 0.85 g of the expected product with a Rf=0.25 in cyclohexane - ethyl acetate (8-2).

STEP G: 2-amino-2-methyl-4-methylene heptanedioic acid 420 mg of the product of Step F were dissolved in 5 ml of ethanol and 1.66 ml of 2N sodium hydroxide were added. The mixture was stirred for 2 hours at ambient temperature and the ethanol was evaporated off. The residue was taken up in 5 ml of 2N sodium hydroxide and the mixture was refluxed with stirring for 20 hours. The solution was concentrated to dryness and the residue was taken up in water and neutralized with 2N hydrochloric acid. The solution was passed through ion-exchange resin Dowex 50 W×8 (H+), eluted with water and then with 0.7N ammonia. The significant fractions were concentrated to dryness and the residue was taken up in 10 ml of water and lyophilized for 16 hours to obtain 250 mg of the expected product with a Rf=0.5 in BuOH—AcOH—$H_2O$ (4-2-2).

NMR Spectrum ($D_2O$) ppm: 3.85: H of the $CH_2$ in position 6; 5.17-5.23 and 5.22-5.27: H of substituted methylene in position 4; 1.54: H of the substituted $CH_3$ in position 2; 2.4 to 2.9: the $CH_2$'s.

EXAMPLE 12

2-amino-2-(difluoromethyl)-4-methylene heptanedioic acid

STEP A: (1,1-dimethylethyl)-1-ethyl-3-(2-methyl-2-propenyl)-propanedioate 33 g of ethyl and tert-butyl malonate were dissolved in 400 ml of acetonitrile, and 29 g of potassium carbonate, 0.5 g of crown ether (18-6) and 300 g of 3-chloro-2-methyl-1-propene were added with stirring. Then, the mixture was stirred for 16 hours at 65° C. and the insoluble part was filtered off. The filtrate was evaporated to dryness and the residue was chromatographed on silica. Elution with a cyclohexane - ethyl acetate mixture (95-5) yielded 18 g of pure product and 22 g of mixture which was chromatographed on silica. Elution with a cyclohexane - ethyl acetate mixture (97.5-2.5) yielded another 11 g of the expected product with a Rf=0.35 in cyclohexane - ethyl acetate (95-5).

STEP B: 1-(1,1-dimethylethyl) and 3 ethyl (difluoromethyl) (2-methyl-2-propenyl)-propanedioate 2.8 g of sodium hydride were suspended in 100 ml of tetrahydrofuran and 11.1 g of the product of Step A in 100 ml of tetrahydrofuran were added dropwise, followed by stirring for one hour at 42° C. Freon 22 was bubbled through for 15 minutes while stirring at 45° C. The mixture was stirred for one hour at 45° C. and one hour at ambient temperature under a Freon 22 atmosphere. The mixture was hydrolyzed with salt water and extracted with methylene chloride, and the organic phase was washed with salt water, dried and concentrated to dryness to obtain 13 g of the expected product with a Rf=0.4 in cyclohexane - ethyl acetate (95-5).

STEP C: Monoethyl (difluoromethyl) (2-methyl-2-propenyl)-propanedioate 13 g of the product of Step B were dissolved in 100 ml of methylene chloride and 70 ml of trifluoroacetic acid were added with stirring for 90 minutes at ambient temperature. After concentration to dryness under reduced pressure, the residue was taken up in methylene chloride and extraction was done with a 10% aqueous solution of sodium bicarbonate. The aqueous phase was washed with methylene chloride and neutralized with concentrated hydrochloric acid. After extraction with methylene chloride, the extracts were washed with salt water, dried and concentrated to dryness to obtain 5.3 g of the expected product with a Rf=0.5 in $CH_2Cl_2$—MeOH—AcOH (9-0.5-0.5).

STEP D: Ethyl 2-(difluoromethyl)-2-(formylamino)-4-methyl-4-pentenoate 10.5 g of the product of Step C in 60 ml of thionyl chloride were refluxed with stirring for 3 hours. After evaporating to dryness, the residue was taken up in toluene and dried under reduced pressure to obtain 10.5 g of acid chloride. The latter was dissolved in 50 ml of acetone and cooled to 0° C. A solution of 3.35 g of sodium azide in 20 ml of water was added dropwise followed by stirring for one hour at 0° C. The acetone was evaporated off, and extraction was done with ether. The extracts were washed with salt water, dried, evaporated to dryness to obtain 10 g of azide.

The latter was dissolved in 100 ml of formic acid and refluxed for 90 minutes. The mixture was allowed to return to ambient temperature and 40 ml of acetic anhydride were added dropwise, followed by stirring for 3 hours at ambient temperature. 40 ml of iced water were added slowly, and the solution was evaporated to dryness. The residue was taken up in a water - methylene chloride mixture, and extracted with methylene chloride. The extracts were washed with a 10% aqueous solution of sodium bicarbonate, then with salt water, dried and concentrated to dryness. The residue was chromatographed on silica and eluted with a cyclohexane - ethyl acetate mixture (85-15) to obtain 5 g of the expected product.

STEP E: Diethyl 2-(fluoromethyl)-2-(formylamino)-6-hydroxy-4-methylene-heptanedioate 9.65 g of ferric chloride were suspended in 50 ml of methylene chloride and 3.03 g of ethyl glyoxylate in 50 ml of methylene chloride were added dropwise, followed by stirring for 30 minutes at ambient temperature. After cooling to −60° C. 3.5 g of the product of Step D in 50 ml of methylene chloride were added dropwise. The mixture was stirred for one hour at −30° C., then for one hour at −20° C. The mixture was poured into iced water and extracted with methylene chloride. The extracts were washed with salt water, with a 10% aqueous solution of sodium bicarbonate, and then with salt water. After drying and evaporating to dryness, the residue was chromatographed on silica and eluted with a cyclohexane - ethyl acetate mixture (6-4) to obtain 0.590 g of product B (4-methyl heptene . . . ), 1.7 g of product C (4-methylene heptane . . . ) and 1 g of mixture. Product B: Rf=0.32 in cyclohexane - ethyl acetate (1-1) Product C: Rf=0.35

STEP F: Diethyl 2-(difluoromethyl)-2-(formylamino)-4-methylene-6-[(methylsulfonyl)-oxy]-heptanedioate 1.65 g of product C of Step E were dissolved in 20 ml of pyridine and after cooling to 0° C., 0.725 g of methanesulfonyl chloride were added.

The mixture was stirred for 30 minutes at 0° C. and for 5 hours at ambient temperature. The mixture was poured into iced 6N hydrochloric acid and extracted with methylene chloride. The organic phase was washed with 6N hydrochloric acid, then with a 10% aqueous solution of sodium bicarbonate and finally with salt water. After drying and evaporating to dryness, the residue was chromatographed on silica and eluted with a methylene chloride - ethyl acetate mixture (9-1) to obtain 1.55 g of the expected product with a Rf=0.45 in CH$_2$Cl$_2$—AcOEt (8-2).

STEP G: Diethyl 2-(difluoromethyl)-2-(formylamino)-4-methylene-heptanedioate 0.430 g of the product of Step F were dissolved in 20 ml of dimethoxyethane and 2 ml of water, and 0.770 g of sodium iodide and 0.670 g of zinc were added. The mixture was refluxed with stirring for 9 hours. After filtering, 25 ml of water were added to the filtrate and extraction was done with methylene chloride. The organic phase was washed with salt water, dried and evaporated to dryness to obtain 300 mg of the expected product with a Rf=0.5 in CH$_2$Cl$_2$—AcOEt (8-2).

STEP H: 2-amino-2-(difluoromethyl)-4-methylene heptanedioic acid 250 mg of the product of Step G were dissolved in 5 ml of ethanol and 0.5 ml of concentrated hydrochloric acid were added. The mixture was refluxed with stirring for one hour, then neutralized with sodium bicarbonate and evaporated to dryness. The residue was taken up in water and extracted with ethyl acetate. The extracts were washed with salt water, dried and evaporated to dryness. The residue was taken up in ethanol and 2.5 ml of 0.1N sodium hydroxide were added. The mixture was stirred for 16 hours at ambient temperature and the medium was neutralized to pH 6 with acetic acid and evaporated to dryness. The residue was taken up in 2 ml of of water and passed through ion-exchange resin Dowex 50 W×8. Elution with water and then with 0.7N ammonia yielded 130 mg of product which was lyophilized in 10 ml of water to obtain 125 mg of the expected product with a Rf=0.6 in BuOH—AcOH—H$_2$O (4-2-2).

NMR Spectrum (ppm): 6.28: CHF; 2.56 and 2.92: CH$_2$ in position 3; 5.06 and 5.11: CH$_2$ of the substituted methylene in position 4.

EXAMPLE 13

2-(L-alanylamino)-3-heptenedioic acid 1.83 g of (2,5-dioxopyrrolidin-1-yl) N-[(1,1-dimethyl ethoxy) carbonyl] L-alaninate were suspended in 10 ml of dimethylformamide cooled to 0° C. and 0.250 g of 2-amino 3-heptenedioic acid in 20 ml of dimethylformamide were added dropwise at a pH between 8 and 9 with triethylamine. The mixture was stirred for 16 hours at ambient temperature, then concentrated to dryness and the residue was dissolved in 10 ml of water. The solution was washed with ethyl acetate, brought to a pH of 1 with 2N hydrochloric acid and extracted with ethyl acetate. The organic phase were dried and the residue was chromatographed on silica. Elution with a mixture of methylene chloride - methanol - formic acid (95-5-1) yielded 0.467 g of blocked product. 0.400 g of the latter were dissolved in 10 ml of trifluoroacetic acid in methylene chloride (1-1) and the mixture stood for an hour at ambient temperature. The mixture was evaporated to dryness and the residue was taken up twice in methylene chloride and evaporated to dryness. The residue was dissolved in water and the solution was adjusted to pH 7 with 2N sodium hydroxide. This solution was passed through Dowex 50 W×8 ion-exchange resin and eluted with 0.2M ammonia to obtain 0.211 g of product which was purified on silica. Elution with ethanol - ammonia (9-1) then (8-2) yielded 108 mg of the expected product after lyophilization.

Preparation of (2,5-dioxopyrrolidin-1-yl) N-[(1,1-dimethylethoxy)-carbonyl]-L-alaninate 0.2 g of B.O.C. L-alanine and 0.122 g of 1-hydroxy 2,5-dioxopyrrolidine were dissolved in 5 ml of dimethoxyethane and the solution was cooled to 0° C. 0.24 g of dicyclohexylcarbodiimide were added little by little and the mixture stood for 7 hours, was filtered and evaporated to dryness. The residue was dissolved in methylene chloride, washed with a 10% aqueous solution of sodium bicarbonate, and dried to obtain 0.305 g of crude product. The latter was crystallized from 1.5 ml of isopropanol to obtain 0.220 g of the expected product melting at 164° C.

EXAMPLE 14

2-(L-lysylamino)-heptanedioic acid 678 mg of 6-(L-lysylamino) 3-heptenedioic acid prepared as in Example 9 were dissolved at ambient temperature in 70 ml of ethanol and 2.1 ml of N hydrochloric acid and then 140 mg of palladium on active carbon were added, followed by hydrogenation under 1100 millibars for an hour and a half. The residue, after filtering, was evaporated to dryness, rinsed with ethanol then with water, dried and concentrated to dryness under reduced pressure. The residue was dissolved in water, and the pH was adjusted to 6 with ammonium hydroxide. The mixture was purified by passing through Dowex 50 W×8 ion-exchange resin and eluting with water and then with 0.5N ammonia, evaporation to dryness and lyophilized to obtain 566 mg of the expected product with a specific rotation of $[\alpha]_D = +29° \pm 1.5°$ (c=0.7% in H$_2$O).

EXAMPLE 15

2-[N-(1-oxo-octadecyl) L-alanyl-γ-D-glutamyl amino]-heptanedioic acid sodium salt

STEP A: 7-ethyl and 1 methyl 6-[oxo-octadecyl)-L-alanyl-γ-D-glutamyl (0-methyl)-amino]-3-heptanedioate For 4 hours, 450 mg of 7-ethyl and 1-ethyl 6-[(N-[(1-oxo-octadecyl) L-alanyl] 0-methyl-γ-D-glutamyl]-amino]-3-heptanedioate prepared as in Example 7 were hydrogenated in 45 ml of methanol in the presence of 45 mg of palladium at 10% on active carbon. After filtering, washing in methanol and concentrated to dryness under reduced pressure, 426 mg of crude product were recovered which was dissolved in 4 ml of tepid methylene chloride and filtered. 2 ml of isopropyl ether were added and the mixture stood for 16 hours at +4° C., was centrifuged and dried under reduced pressure to obtain 375 mg of the expected product melting at ≈100° C. and having a specific rotation of $[\alpha]_D = -16° \pm 1°$ (c=0.9% in CH$_2$Cl$_2$).

NMR Spectrum (CDCl$_3$) ppm: CH$_3$ of the chain: 0.88; (CH$_2$)$_n$ and CO$_2$CH—CH$_3$: 1.26; CH$_3$—CH: 1.39; the CO$_2$—CH$_3$: 3.66 and 3.73; CO$_2$—CH$_2$—CH$_3$: 4.20; NH—CH—C=O: 4.35 to 4.60;

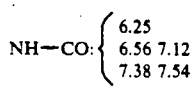

STEP B:
2-[N-(1-oxo-octadecyl)-L-alanyl-γ-D-glutamyl amino]heptanedioic acid, sodium salt 0.66 ml of N sodium hydroxide were added dropwise to a solution of 140 mg of the product of Step A in 2.8 ml of ethanol and the mixture was stirred for 16 hours at ambient temperature. The mixture was evaporated to dryness under reduced pressure and the residue was dissolved in water and lyophilized to obtain 136 mg of the expected product with a specific rotation of $[\alpha]_D = -21°\pm1°$ (c=0.5% in $H_2O$).

NMR Spectrum ($D_2O$) ppm: $CH_3$ of the chain 0.90; $(CH_2)_n$ and $CH_2$ in alpha of $CO_2Na$: 1.29; $CH_3$—CH: 1.39;

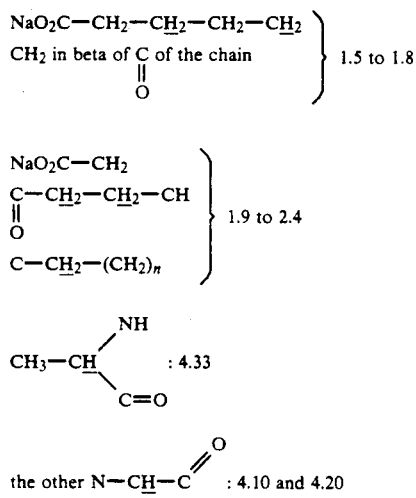

EXAMPLE 16
6-[(4-hydroxy 1,4-dioxobutyl)-amino]-3-heptenedioic acid

STEP A: (7) ethyl and of (1) methyl 6-[(1,4-dioxo-4-ethoxybutyl)-amino]-3-heptenedioate 338 mg of triethylamine were added at ambient temperature to 583 mg of 1-methyl 7-ethyl 6-amino-3-heptenedioate prepared as in Example 5D in 50 ml of methylene chloride and after the mixture was cooled to +5° C., 483 mg of ethyl 4-chloro-4-oxo-butanoate were added. The mixture was stirred for 1 hour at ambient temperature and 25 ml of water and 1 ml of 2N hydrochloric acid were added. Extraction was done with methylene chloride and the extract was washed with salt water, then with sodium bicarbonate solution, dried and the solvents were evaporated. The residue was chromatographed on silica and elution with cyclohexane - ethylene acetate (1-1) yielded 750 mg of the expected product.

NMR Spectrum $CDCl_3$ (250 Mhz) ppm: H of the ethylenics: 5.43-5.64; H of $H_3CO_2C$: 4.23-3.69; H of $CH_2$—CH=CH: 3.06; H of the $CO_2Et$: 1.26 and 1.28-4.10 to 4.25; H of the $CH_2$: 2.4 to 2.7.

STEP B: 6-[(4-hydroxy 1,4-dioxobutyl)-amino]-3-heptenedioic acid 4.66 ml of N sodium hydroxide solution were added to 500 mg of the product of Step A in 10 ml of ethanol and the mixture was stirred for 16 hours at ambient temperature and was then treated with Amberlyst 15 resin to pH of 6. The extract was filtered and the filtrate was concentrated to dryness. The residue was dissolved in 30 ml of water, filtered and lyophylized to obtain 470 mg of the expected product.

NMR Spectrum $D_2O$ (250 MHz) ppm: H of the ethylenics: 5.50 and 5.65; H of —CH—NH: 4.23; H of $HO_2C$—$CH_2$: 3.02; H of $CH_2$—CH—$CH_2$: 2.35 to 2.6.

EXAMPLE 17
6-[[N-(1-oxo-octadecyl)γ-D-glutamyl]-amino]-3-heptenedioic acid (sodium salt)

STEP A: Ethyl 6-[[N-(1-oxo-octadecyl)γ-D-glutamyl]-amino-3-heptenedioate 1.28 g of 4-[N-1-oxo-octadecyl]-glutamic acid in a mixture of dioxane-tetrahydrofuran (3-1) were cooled to 14° C. and then over 5 minutes, 0.86 ml of triethylamine and then 0.43 ml of isobutyl chloroformate were added. The mixture was stirred for 35 minutes at 14° C. and then 647.8 mg of 1-methyl-7-ethyl-6-amino-3-heptenedioate of 1-methyl-7-ethyl as prepared in Example 5D in 15 ml of tetrahydrofuran were added. The mixture was stirred for 2 hours at ambient temperature and then was chromatographed on silica. Elution with methylene chloride-methanol 98-2 yielded 980 mg of crude product which was dissolved in 3 ml of methylene chloride. 1 ml of isopropyl ether was added, and after crystallization for 16 hours at +5° C., and drying under reduced pressure at ambient temperature, 840 mg of the expected product were obtained which had a specific rotation $[\alpha]_D = +8°\pm1°$ (c=1% in pyridine).

NMR Spectrum ($CDCl_3$) (250 MHz) ppm: $CH_3$—$(CH_2)_n$: 0.88; $(CH_2)_n$ and $CH_3$ of OEt: ≈1.25; $CH_2$—C= and $CH_2C$=O: 2.1 to 2.6; the OMe: 3.68 and 3.74; $CH_2$ of $CO_2Et$: 4.20; N—CH—C=O: 4.62; ethylenics: 5.45 to 5.65;

the NH—C: 6.56
‖
O 6.76

STEP B: 6-[[N-(1-oxo-octacdecyl)γ-D-glutamyl]-amino]-3-heptenedioic acid (sodium salt)

2.1 ml N sodium hydroxide were added at 0° C. to 400 mg of the product of Step A suspended in 10 ml of ethanol and the mixture was stirred for 16 hours at ambient temperature. The mixture was concentrated under reduced pressure and the residue was dissolved in 10 ml of water, filtered and lyophilized to obtain 370 mg of the expected product with a specific rotation of $[\alpha]_D = -13°\pm1°$ (c=1% in $H_2O$).

NMR Spectrum ($D_2O$ 300 MHz)ppm: CH—$CH_2$—CONa: 2.93; the CH ethylenics: 5.43-5.67; the $CH_2$: 1.8-2.6; CH—NH: 4.18; $CH_3$: 0.86.

EXAMPLE 18

6-[(γ-D-glutamyl)-amino]-3-heptenedioic acid

STEP A: Ethyl 6-[(N-trifluoroacetyl-γ-D-glutamyl)-amino]-3-heptenedioate

Over 15 minutes a solution of 554 mg of glutamic acid in 30 ml of dimethoxyethane was added to 422 mg of the product of Step D of Example 5. The solution was cooled to 0° C., and over 10 minutes, a solution of 475 mg of dicyclohexylcarbodiimide in 10 ml of dimethoxyethane was added. The suspension was stirred for 16 hours at 0° C., then for 4 hours at ambient temperature and filtered. The filtrate was evaporated to dryness and the oily residue was dissolved in 10 ml of ether, filtered and evaporated to dryness. 1.03 g of the crude product recovered were purified by chromatography on silica (eluent cyclohexane - ethyl acetate 5-5) to obtain 410 mg of the expected product.

NMR Spectrum (CDCl$_3$) 250 MHz: CO$_2$Et: 1.29 (t) -4.21 (p); CH$_2$=: 2 to 2.66; CH—CO$_2$CH$_3$: 3.06 (d); CO$_2$—CH$_3$: 3.69-3.77 and 3.78;

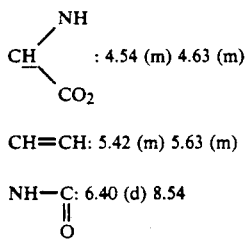

CH=CH: 5.42 (m) 5.63 (m)

NH—C: 6.40 (d) 8.54
‖
O

STEP B: 6-[(γ-D-glutamyl)-amino]-3-heptenedioic acid 454 mg of the product of Step A were dissolved in 20 ml of ethanol cooled to 0° C. and 3.6 ml of N sodium hydroxide were added. The mixture was stirred while 1 ml of water was added and stirring was continued for 16 hours at ambient temperature. After concentrating under reduced pressure, the residue was dissolved in 2 ml of water and the pH was adjusted to 6 by a 2N hydrochloric acid solution. The mixture was purified by passing it over Dowex (50 W × 8) resin and eluting with water, then with ammonia to obtain 272 mg of the product which was dissolved in 10 ml of water, then lyophilized to obtain 215 mg of the expected product with a specific rotation of $[\alpha]_D = -18° \pm 2°$ (c=0.5% in HCl$_6$N).

NMR Spectrum (D$_2$O) 300 MHz ppm: CH$_2$—CO$_2$H: 2.95 (d, gamma=7H$_2$); CH=CH: 5.64 (d, J=15.5 and 7H$_2$) 5.49;

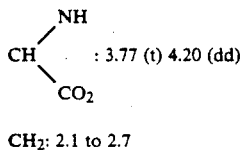

CH$_2$: 2.1 to 2.7

EXAMPLE 19 and 20

Tablets were prepared 50 mg containing of the product of Example 2 or 6 and sufficient excipient of lactose, starch and talc, magnesium stearate for a final weight of 250 mg.

PHARMACOLOGICAL STUDY

Stimulation of the Monocyte Cells by an Immuno-Stimulant

The mononucleus cells of the circulating blood of normal donors were separated according to the standard technique described by Boyum using a Ficoll gradient. After washing, the mononuclear cells were incubated at 37° C. for one hour at the rate of 5.10$^6$ monocytes (NSE+ cells) per ml of culture medium using 5 ml per culture flask. The culture medium used in this experiment was made up of RPMI 1640 with the addition of antibiotics and Hepes buffer. After one hour, the non-adherent cells were removed by washing the flasks with medium previously heated to 37° C. and the adherent cells composed mostly of monocytes (>90%) were put back in culture in complete RPMI medium without serum in the presence of various quantities of products under test, which had previously been put in solution in a buffer (Dulbecco) without Ca$^{2+}$ or Mg$^{2+}$. The culture was continued for 24 or 48 hours and the supernatants of the cells were then removed, centrifuged, separated into equal lots and held either at -80° C. or at -20° C. The supernatants of the culture were replaced in the flasks by the same amount of apyrogenous distilled water to dissolve the cells. The lysate was recovered, separated into equal lots and also kept at -20° C. The following experiments were carried out in the presence of or in the absence of gamma Interferon (10$^3$ U/ml) at a dose where only the gamma IFN was inactive.

Tests for the Presence of Monokines (Interleukine-1 and Tumor Necrosis Factor) in the Supernatants, by Their Biological Activity

Interleukine-1 (IL-1) Test

This test was described for the first time by Gery et al in 1972 [Gery et al 1972. Potentiation of the T lymphocyte response to mitogens. II. The cellular source of potentiating mediator (s) J. Exp. Med., 136-143]. It is based on the co-mitogen action of IL-1 in the presence of an antigen (mimicked by phytohemaglutinine in the test) on the thymocytes of mice. 1.5 × 10$^6$ thymocytes of mice C3H/HeJ (from the C.S.E.A.L. of Orleans) were put in culture for three days in the presence of various dilutions of supernatants and of cell lysates which may contain IL-1 activity and of PHA-P Wellcome (1 ug/ml) in culture plates with 96 flat bottomed wells, in a final volume of 200 ul of medium composed of RPMI 1640 containing in addition to antibiotics (penicillin 1 U/ml - streptomycin 1000 U/ml) of Hepes buffer, 1 mM of glutamine, 2 mM 5% of calf serum and 5 × 10$^5$M of 2-mercapto ethanol. After 68 hours of culture, 1 μCi of tritiated thymidine was added to each well ($^3$H-methyl thymidine, CEA Saclay, TMM79A specific activity 1 Ci/mM=37 GBq/mM) and the radioactivity incorporated by the cells was evaluated after the cultures had been filtered on Skatron type semi-automatic collecting apparatus and the filters had been counted in a liquid scintillation counter (Beckman). The results were expressed by the difference between the impulses per minute incorporated by the cultures in the presence of supernatants and the impulses per minute incorporated by the control cultures.

Tumor Necrosis Factor (TNF) Test

The TNF activity is shown by the toxicity of this factor on the L-929 target cells (sub-clone alpha) and the technique was sensitized by adding D actinomycin in the test. The L cells were distributed at a rate of $2 \times 10^4$ cells per well of a flat-bottomed microplate in 100 μl of RPMI 1640 medium enriched with 5% of calf serum, glutamine, Hepes buffer and antibiotics. After 24 hours, various dilutions of the supernatants under test were added in a volume of 100 μl, as well as a dose of D actinomycin of 1 μg/ml. After 24 hours of culture, the quantity of undissolved cells was evaluated by coloring the plates with crystal violet and measuring the optical density of the different wells on a multiscan reader. RESULTS: The product of Example 9 stimulated the monocytes and their production of IL-1 and TNF. Furthermore, there was synergy between the products and the gamma Interferon.

B. Antibacterial Activity (in Vitro)

The antibacterial activity of the products was determined by the method of diffusion in a Davis Mingioli medium with 1% of agar added to it. The agars used were poured into Petri dishes at 48° C., after inoculating with $5 \times 10^{-5}$ germs/ml with the bacterial strain under test. The inocula came from a culture made 24 hours earlier in a Davis Mingioli broth. After the agars had hardened, the aqueous solutions of the products being studied were introduced into wells (9 mm) hollowed in the medium with a punch. The inhibition zones observed (diameter in mm) were measured after incubation for 24 hours at 37° C.

|  | Product of example 6 (25 mg/l) | Product of example 13 (25 mg/l) |
| --- | --- | --- |
| *Escherichia Coli* O78 |  | 17.5 |
| *Salmonella typhimurium* MZ11 | 24 | 20 |
| *Enterobacter cloacae* 1321E | 10 |  |
| Providencia sp. DU48 |  | 22 |

C. Antibacterial Activity (in Vivo)

Swiss female mice weighing from 18 to 20 g (Charles River Cobs noninbred CD1) were used for this experiment with each group comprising 20 animals. The various products were put in solution in apyrogenous physiological serum to obtain concentrations of 1-10-100 mcg/mouse or: 50-500-5000 mcg/kg.

Preparation of the Infectant Suspension (Strain IP 52 145)

(A) Preservation and Maintanence of the Strain

The lyophilized strain was re-hydrated with a few drops of soja trypcase broth (BioMerieux) and a tube of 10 ml of soja trypcase broth was inoculated with the suspension obtained and cultivated for 18 hours in an incubator at 37° C. Tubes of preserving agar (Pasteur) were inoculated with this culture by central stabing. After 18 hours of culture in an incubator at 37° C., the tubes were kept at 22° C.

(B) Culturing

A tube of soja trypcase broth was inoculated from a preserving agar and cultivated for 18 hours in an incubator at 37° C. Inclined soja trypcase agars were inoculated from this culture. After 18 hours of incubation at 37° C., the germs were recovered on the surface of the agar and put in suspension in physiological serum at a rate of one platinum loop for 10 ml of physiological water. The germ concentration was evaluated by counting with a Coulter Counter. The bacterial suspension was diluted until the desired dose of germs was obtained, then injected by intravenous route in a volume of 0.2 ml/mouse. The quantity of revivable germs injected was checked by spreading on Petri dishes containing trypcase agar.

Protocol

Administration was done with an intramuscular injection in a volume of 0.05 ml/mouse 24 hours before infection. The germs were injected by intravenous route in a volume of 0.2 ml/mouse. The animals were observed for 21 days and a comparison was made of the mortality of untreated animals (control) to that of animals treated with the various products. The results were expressed in terms of survival (number of animals surviving in each group at the end of the 21 days of observation). The Fisher test was used to compare the survivals of the treated groups with the control group. Where a clear increase in survival could not be detected after 21 days of observation, an average survival time (AST) was calculated for each group. In this case, the statistical analysis was made by the Mann and Whitney test, comparing each of the groups treated with the control group.

The study was carried out on an IBM PC computer and a Tadpole program. A particularly significant protection was observed in the group treated by the product of Example 8 at a dose of 5 mg/kg: results expressed in AST or in survival at the end of 21 days of observation.

D. Activity on Human Monocytes

The products of Examples 5 and 9 showed a direct effect on human monocytes, which effect was measured by the production of a TNF activity and of an IL-1 activity in the culture supernatants (with 5 g of product). Furthermore, with the product of Example 9, in the presence of CHU—IFN—g, it was possible to show an effect which at least increased the production of monokines (TNF and IL-1).

Various modifications of the products and methods of the invention may be made without departing from the spirit or scope thereof and it is to be understood that the invention is intended to be limited only as defined in the appended claims.

What we claim:

1. A compound selected from the group consisting of (A) compounds of the formula

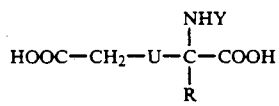

wherein U is

m and n are individually 1 or 2, the dotted lines are a single double bond optionally of cis or trans configuration, a is selected from the group consisting of hydrogen, methyl and methylene, Y is selected from the group consisting of hydrogen, residue of an amino acid with an α- or ω- carboxyl selected from the group consisting of Ala, Val, Ival, Leu, Ile, Asp, Asn, Glu, Gln, Ser, Thr, Cys, Met, Lys, Arg, Phe, Tyr, Trp, His and Pro, Nva, Nle, Hyp, Orn with the acids being in the D or L form as well as Sar and Gly and a peptide of 2, 3 or 4 of the said amino acids with the amine optionally acylated with an optionally unsaturated aliphatic carboxylic acid of 6 to 24 carbon atoms or alkylated with alkyl of 1 to 8 carbon atoms, R is selected from the group consisting of hydrogen, alkyl of 1 to 8 carbon atoms, alkenyl and alkynyl of 2 to 8 carbon atoms optionally substituted with at least one halogen with the proviso that if Y is hydrogen, alanine or proline and if a is hydrogen, U contains a double bond; and (B) their non-toxic, pharmaceutically acceptable salts with bases or acids, the alkyl esters of 1 to 6 carbon atoms and their primary and secondary amides.

2. A compound of claim 1 wherein U is —CH=CH—CH$_2$— or —CH$_2$—CH=CH—.

3. A compound of claim 1 wherein Y is a residue of a compound selected from the group consisting of alanine, proline, lysine and alpha and gamma glutamic acid.

4. A compound of claim 1 wherein Y is a residue of alanine.

5. A compound of claim 1 wherein Y is a residue of lysine.

6. A compound of claim 1 wherein R is a hydrogen.

7. A compound of claim 1 wherein R is methyl.

8. A compound of claim 1 wherein R is —CHF$_2$ or ethynyl or vinyl.

9. A compound of claim 1 selected from the group consisting of 6-(L-lysylamino)-3-heptenedioic acid, esters with alcohols of 1 to 6 carbon atoms, salts with non-toxic, pharmaceutically acceptable bases and its primary and secondary amides.

10. A compound of claim 1 selected from the group consisting of 6-[L-alanylamino]-3-heptenedioic acid, 2-[L-alanylamino]-3-heptenedioic acid, 2-[N-(1-oxo-octadecyl)-L-alanyl-γ-D-glutamyl-amino]-heptanedioic acid and 6-[(4-hydroxy-1,4-dioxobutyl)-amino]-3-heptenedioic acid, esters with alcohols of 1 to 6 carbon atoms, salts with non-toxic, pharmaceutically acceptable bases and its primary and secondary amides.

11. An antibacterial composition comprising an antibacterially effective amount of at least one compound of claim 1 and an inert pharmaceutical carrier.

12. A composition of claim 11 wherein U is —CH=CH—CH$_2$— or —CH$_2$—CH=CH—.

13. A composition of claim 11 wherein Y is a residue of a compound selected from the group consisting of alanine, proline, lysine and alpha and gamma glutamic acid.

14. A composition of claim 11 wherein Y is a residue of alanine.

15. A composition of claim 11 wherein Y is a residue of lysine.

16. A composition of claim 11 wherein R is hydrogen.

17. A composition of claim 11 wherein R is methyl.

18. A composition of claim 11 wherein R is —CHF$_2$ or ethynyl or vinyl.

19. A composition of claim 1 wherein the active compound is selected from the group consisting of 6-(L-lysylamino)-3-heptenedioic acid, esters with alcohols of 1 to 6 carbon atoms, salts with non-toxic, pharmaceutically acceptable bases and its primary and secondary amides.

20. A composition of claim 1 wherein the active compound is selected from the group consisting of 6-[L-alanylamino]-3-heptenedioic acid, 2-[L-alanylamino]-3-heptenedioic acid, 2-[N-(1-oxo-octadecyl)-L-alanyl-γ-D-glutamyl-amino]-heptanedioic acid and 6-[(4-hydroxy-1,4-dioxobutyl)-amino]-3-heptenedioic acid, esters with alcohols of 1 to 6 carbon atoms, salts with non-toxic, pharmaceutically acceptable bases and its primary and secondary amides.

21. A method of combatting bacterial infections in warm-blooded animals comprising administering to warm-blooded animals an antibacterially effective amount of at least one compound of claim 1.

22. A method of claim 21 wherein U is —CH=CH—CH$_2$— or —CH$_2$—CH=CH—.

23. A method of claim 21 wherein Y is a residue of a compound selected from the group consisting of alanine, proline, lysine and alpha and gamma glutamic acid.

24. A method of claim 21 wherein Y is a residue of alanine.

25. A method of claim 21 wherein Y is a residue of lysine.

26. A method of claim 21 wherein R is hydrogen.

27. A method of claim 21 wherein R is methyl.

28. A method of claim 21 wherein R is —CHF$_2$ or ethynyl or vinyl.

29. A method of claim 21 wherein the active compound is selected from the group consisting of 6-(L-lysylamino)-3-heptenedioic acid, esters with alcohols of 1 to 6 carbon atoms, salts with non-toxic, pharmaceutically acceptable bases and its primary and secondary amides.

30. A method of claim 21 wherein the active compound is selected from the group consisting of 6-[L-alanylamino]-3-heptenedioic acid, 2-[L-alanylamino]-3-heptenedioic acid, 2-[N-(1-oxo-octadecyl)-L-alanyl-γ-D-glutamyl-amino]-heptanedioic acid and 6-[(4-hydroxy-1,4-dioxobutyl)-amino]-3-heptenedioic acid, esters with alcohols of 1 to 6 carbon atoms, salts with non-toxic, pharmaceutically acceptable bases and its primary and secondary amides.

* * * * *

UNITED STATES PATENT AND TRADEMARK OFFICE
CERTIFICATE OF CORRECTION

PATENT NO. : 5,030,715
DATED : July 9, 1991
INVENTOR(S) : CONSTANTIN AGOURIDAS: PATRICK FAUVEAU AND CHANTAL DAMAIS It is certified that error appears in the above-identified patent and that said Letters Patent is hereby corrected as shown below:

Col. 29, line 22, (claim 2) "-CH= should be -- -CH=CH-CH$_2$-- CH-CH$_2$"

Col. 29, line 52, (Claim 12) should read same as (claim 2)

Col. 30, line 28, (Claim 22) should read sams as (claim 2)

Signed and Sealed this

Twenty-sixth Day of January, 1993

Attest:

STEPHEN G. KUNIN

*Attesting Officer*   Acting Commissioner of Patents and Trademarks